(12) United States Patent
Pagani

(10) Patent No.: US 10,876,999 B2
(45) Date of Patent: Dec. 29, 2020

(54) BLOCK MADE OF A BUILDING MATERIAL

(71) Applicant: STMicroelectronics S.r.l., Agrate Brianza (IT)

(72) Inventor: Alberto Pagani, Nova Milanese (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 0 days.

(21) Appl. No.: 16/415,973

(22) Filed: May 17, 2019

(65) Prior Publication Data

US 2019/0271664 A1 Sep. 5, 2019

Related U.S. Application Data

(62) Division of application No. 15/426,747, filed on Feb. 7, 2017, now Pat. No. 10,330,640, which is a division of application No. 14/027,940, filed on Sep. 16, 2013, now Pat. No. 9,606,085.

(30) Foreign Application Priority Data

Sep. 25, 2012 (IT) ............................. MI2012A1595

(51) Int. Cl.
*G01N 27/72* (2006.01)
*G01N 27/82* (2006.01)
*G01N 33/38* (2006.01)

(52) U.S. Cl.
CPC ............ *G01N 27/82* (2013.01); *G01N 27/72* (2013.01); *G01N 33/381* (2013.01); *G01N 33/383* (2013.01); *Y10T 29/4902* (2015.01); *Y10T 29/49018* (2015.01)

(58) Field of Classification Search
CPC ....... G01N 27/82; G01N 27/72; G01N 33/381
See application file for complete search history.

(56) References Cited

U.S. PATENT DOCUMENTS

| 4,682,111 A | 7/1987 | Hughes | |
|---|---|---|---|
| 7,347,101 B2 * | 3/2008 | Thomson | ................ E01D 19/00 73/773 |
| 7,551,058 B1 * | 6/2009 | Johnson | ............... G01N 27/226 340/10.41 |

(Continued)

FOREIGN PATENT DOCUMENTS

| CN | 1476535 A | 2/2004 |
|---|---|---|
| CN | 203747517 U | 7/2014 |
| WO | 2012084295 A1 | 6/2012 |

OTHER PUBLICATIONS

Finocchiaro et al., "A 900-MHz RFID System with TAG-Antenna Magnetically-Coupled to the Die," IEEE Radio Frequency Integrated Circuits Symposium, 2008, pp. 281-284.

(Continued)

*Primary Examiner* — Reena Aurora
(74) *Attorney, Agent, or Firm* — Slater Matsil, LLP

(57) ABSTRACT

A building structure includes a block of building material and a magnetic circuit buried in the block of building material. The structure also includes a plurality of sensing devices buried in the block of building material. Each sensing device may include a contactless power supplying circuit magnetically coupled with the magnetic circuit to generate a supply voltage when the magnetic circuit is subject to a variable magnetic field.

26 Claims, 16 Drawing Sheets

(56) References Cited

U.S. PATENT DOCUMENTS

| | | | |
|---|---|---|---|
| 7,673,501 B2* | 3/2010 | Holyoake | G01N 27/048 73/73 |
| 9,097,637 B2 | 8/2015 | Pagani et al. | |
| 9,778,117 B2* | 10/2017 | Pagani | G01L 25/00 |
| 2004/0046550 A1 | 3/2004 | Kondo | |
| 2004/0153270 A1 | 8/2004 | Yamashita et al. | |
| 2009/0033467 A1 | 2/2009 | Finocchiaro et al. | |
| 2012/0161789 A1 | 6/2012 | Girlando et al. | |
| 2014/0084909 A1 | 3/2014 | Pagani | |

OTHER PUBLICATIONS

Jiang et al., "Effects of Periodic Reinforced-Concrete Structures on Power Transmissions," IEEE International Conference on RFID, Apr. 2012, pp. 16-23.

* cited by examiner

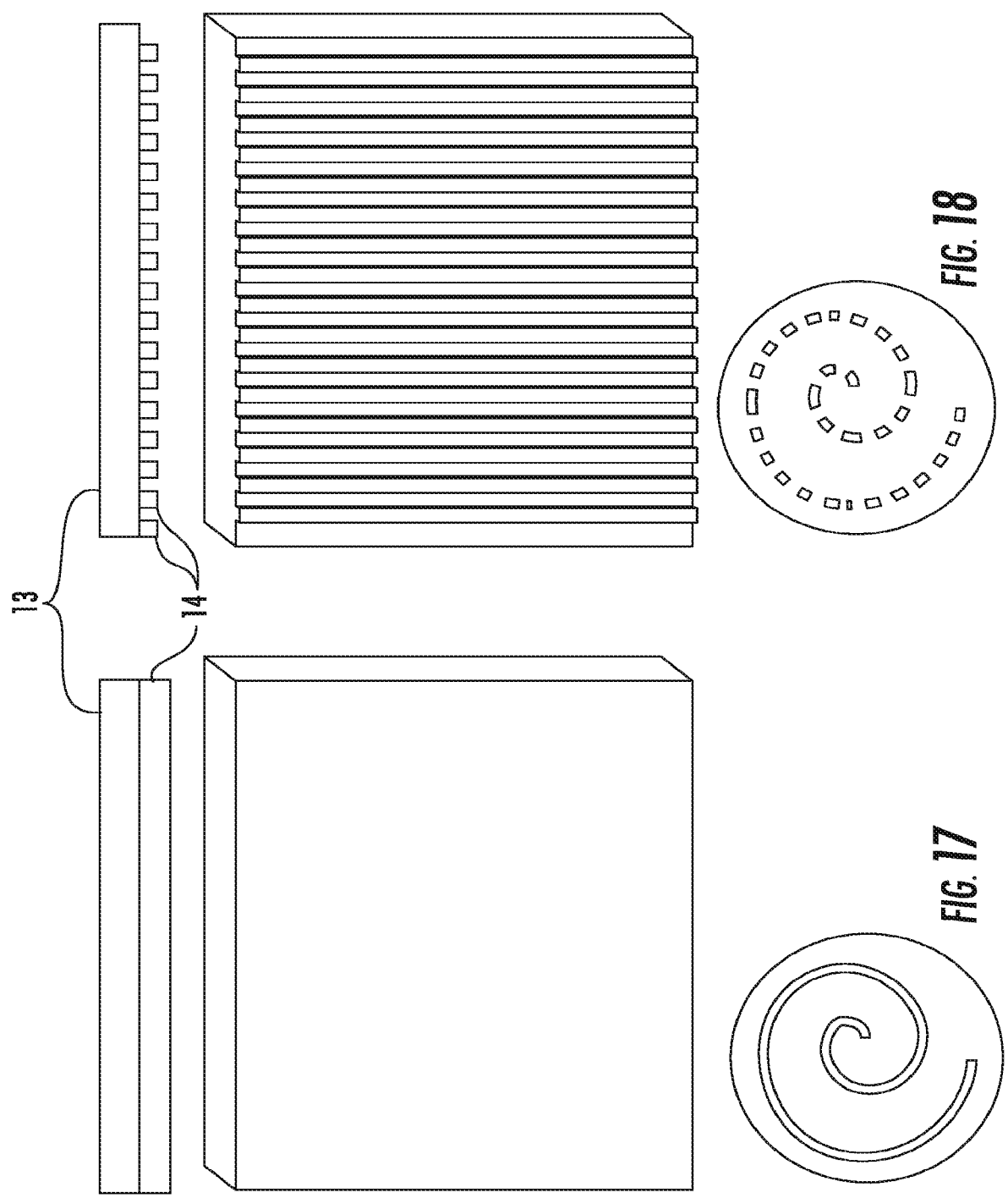

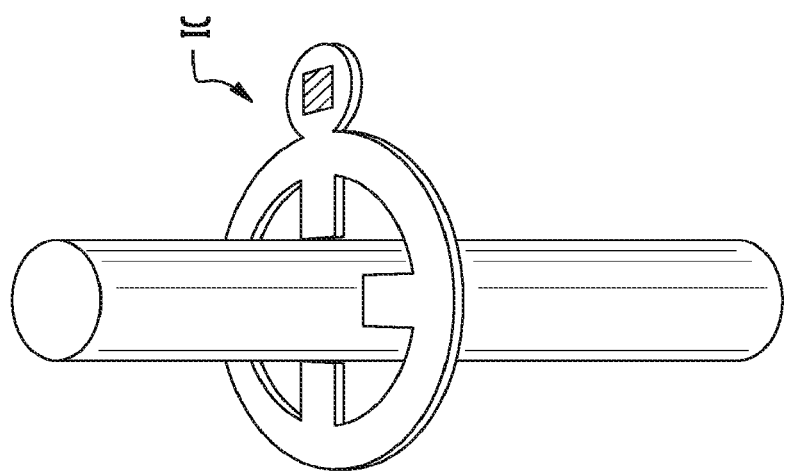
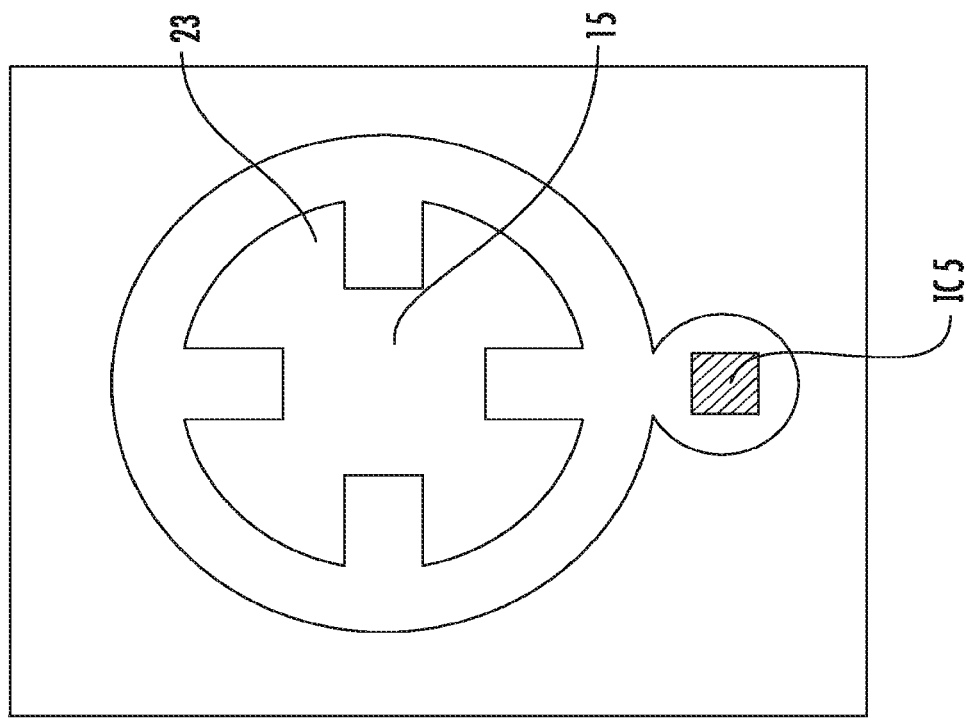
FIG. 24

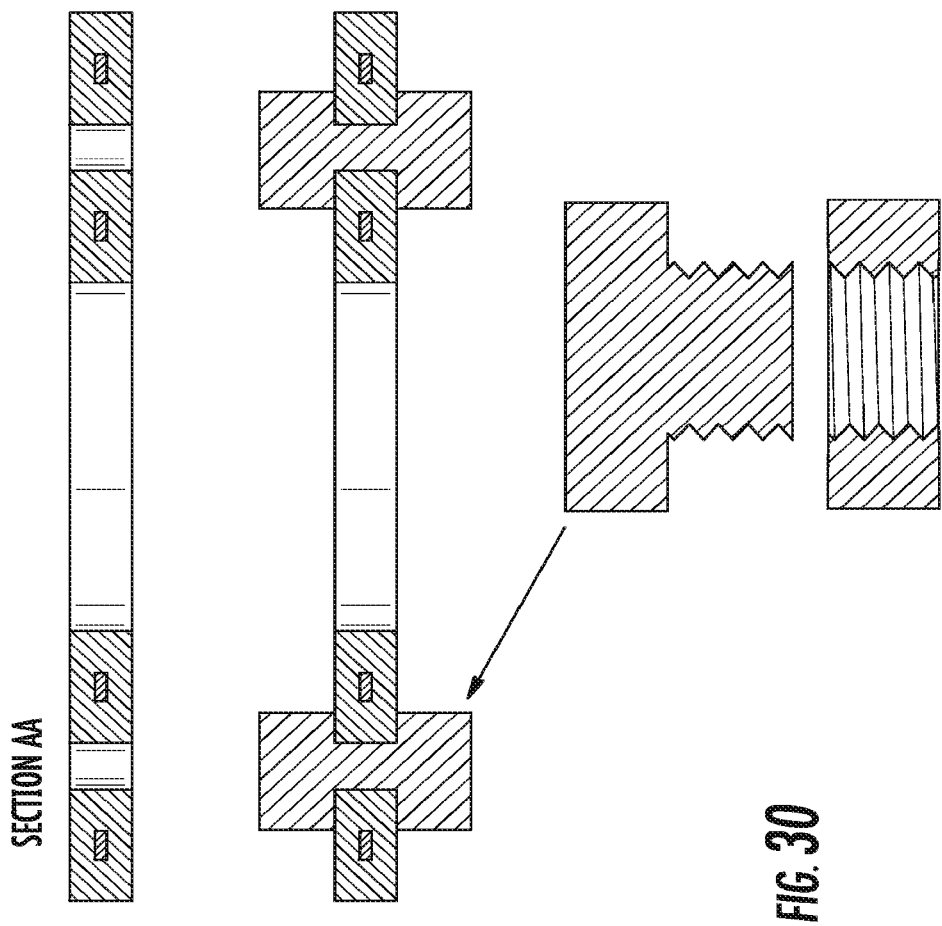
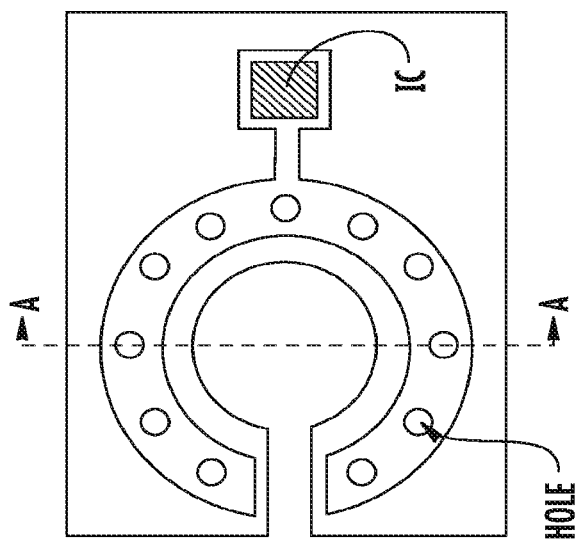
FIG. 30

BLOCK MADE OF A BUILDING MATERIAL

CROSS-REFERENCE TO RELATED APPLICATIONS

This application is a divisional application of U.S. patent Ser. No. 15/426,747, filed on Feb. 7, 2017, which is a divisional of U.S. patent application Ser. No. 14/027,940, filed on Sep. 16, 2013, now issued as U.S. Pat. No. 9,606, 085, which application claims the benefit of Italian Patent Application No. MI2012A001595, filed on Sep. 25, 2012, which applications are hereby incorporated herein by reference.

TECHNICAL FIELD

This invention relates to monitoring devices in building structures, and, more particularly, to a block made of a building material comprising a magnetic circuit to which sensing devices of at least one physical characteristic of the building material are magnetically coupled.

BACKGROUND

The strategy for implementing damage detection and the characterization of mechanical structures is commonly called Structural Health Monitoring (SHM). Damages are defined as modifications of the material and/or of the geometrical properties of a structural system, comprising modifications of boundary conditions and connections of the system, that worsen performance of the system. The SHM process implies the observation of the mechanical system along the time using periodically: measurements of dynamic responses coming from an array of sensors, extraction of data of damage characteristics sensed from these measurements, and statistical analysis of these data of characteristics for determining the present health state of the system (also called structural analysis).

The results (periodically updated) of this process provide information about the capacity of the structure for carrying out its function, considering the unavoidable aging and degradation in working environments. After extreme events, such as earthquakes or explosions, the SHM is used for a quick screening of the conditions of the structure for providing, almost in real time, reliable information about the integrity of the structure itself.

Nowadays, SHM systems use sensors placed on the surfaces to be controlled. For example, sensors used (anemometers for calculating the wind speed, accelerometers, extensometers, motion transducers, temperature sensors, sensors for detecting motion of weights, etc.) for monitoring bridges are placed on the external surfaces of beams, wire ropes or pillars, in order to: estimate the effects of loads on the bridge, evaluate the weakening of the bridge, and foresee the probable evolution of the bridge and its expected lifetime.

SHM systems have been devised with sensing devices including sensors (that for example may measure pressure, humidity, temperature, etc.) adapted to be buried in the structures to be monitored. These devices have at least one remote powering and transmission antenna for transmitting the measured values outside of the block of building material, as in RFID devices (that are sensorless) illustrated in the article by A. Finocchiaro, G. Ferla, G. Girlando, F. Carrara e G. Palmisano, "A 900-MHz RFID System with TAG-Antenna Magnetically-Coupled to the Die", 2008 IEEE Radio Frequency Integrated Circuits Symposium, pages 281-284. This kind of sensing devices is disclosed, for example, in the US Patent applications No. 2004/0153270, 2012/0161789 and 2009/0033467 and in the PCT publication WO 2012/084295, herein incorporated by reference, and are depicted in FIGS. 1, 2, 3 and 4.

In order to supply the buried sensor even in structures of great size, it is known to use power supply shielded electric lines or devices, equipped with a receiving antenna and a transmitting antenna, that act as connections for transmitting in a contactless fashion, at a remote distance electromagnetic energy, required for powering the buried sensors. These shielded electric lines and the devices that act as contactless connections are buried in the cover portion (concrete cover or abutment stone) because the electromagnetic waves are strongly dampened even by relatively thin layers of concrete as well as by reinforcing bars buried in the building structure of reinforced concrete. Without them, it may not be possible to allow the remote powering antennas of the sensing devices buried in blocks of building material to receive an electromagnetic field of sufficient intensity for operating the sensing devices.

An inconvenience tied to the use of these buried devices is the limited reliability of the electric connections used for supplying them. In particular, in the building structures of great size, such as bridges, the electric or contactless power supply connections of the buried sensors may degrade along the time or may be damaged during catastrophic events.

As schematically shown in FIG. 5, that refers to the displacement of sensors and of contactless power supply connections disclosed in the PCT application WO 2012/084295 and the US Patent publication No. 2009/0033467 in the name of the same applicant, these contactless connections are typically buried in the cover portion. The cover portion is the portion of a building structure that more likely is damaged in case of fire or earthquake. Thus the electric connections and/or the contactless devices buried therein may be damaged just when, after a catastrophic event, it may be important to have them function correctly for powering the buried sensor and thus for having information about damage of the structure.

SUMMARY

It may be desirable to be able to supply sensing devices, galvanically isolated and powerable in a contactless fashion, for example, of the type disclosed in the US Patent application No. US 2009/0033467 or the Italian Patent application No. ITMI20102365 or PCT application WO 2012/084295 in the name of the same applicant, buried in relatively large building structures, without having to bury in the cover portion contactless devices or electric supply lines or antennas of these sensing devices.

In order to address this problem, a block of building material has been realized in which there is a magnetic circuit, made of a material adapted to convey a variable magnetic field induced therethrough. In the block there are also a plurality of buried sensing devices galvanically isolated and powerable in a contactless fashion, having sensors for sensing at least one characteristic of the building material, all equipped with respective contactless power supply circuits configured to be magnetically coupled to the magnetic circuit and to generate by induction a supply voltage of the sensor when the magnetic circuit conveys a variable magnetic field.

With an external excitation coil or also with a tool of the type used in magnetometers shaped as a horseshoe on which an excitation coil is wound, it is possible to induce from the outside of the block a variable magnetic field in the internal magnetic circuit. This variable magnetic field, conveyed along the whole magnetic circuit or at least along a portion thereof, allows buried sensors to be supplied at relatively great distances from the excitation coil.

According to an embodiment, the magnetic circuit comprises steel bars soldered among them and eventually coated with a layer of soft-magnetic material.

According to an embodiment, an excitation coil is wound on a portion of the magnetic circuit that protrudes out of the block, and is configured to induce a variable magnetic field in the magnetic circuit.

According to another embodiment, the magnetic circuit is wholly buried and the excitation coil is wound on a portion of the magnetic circuit and is buried in the block and has connection terminals that protrude therefrom.

BRIEF DESCRIPTION OF THE DRAWINGS

FIGS. 17 and 18 show sheets of isolating material respectively fully or striped coated with a magnetic or soft-magnetic material, adapted to be rolled-up for providing a magnetic circuit to be buried in the block according to this disclosure.

FIGS. 21 to 30 show different embodiments of sensing devices that may be coupled to the magnetic circuit buried in the block according to this disclosure.

DETAILED DESCRIPTION OF ILLUSTRATIVE EMBODIMENTS

Figure 1:
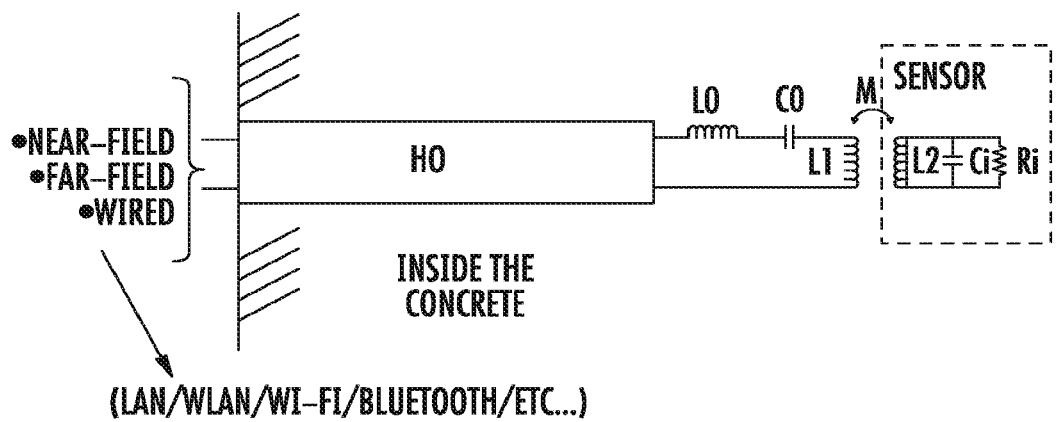
FIG. 1 shows a shielded line adapted to supply a buried sensor in a building material as in the prior art.
Figure 2:
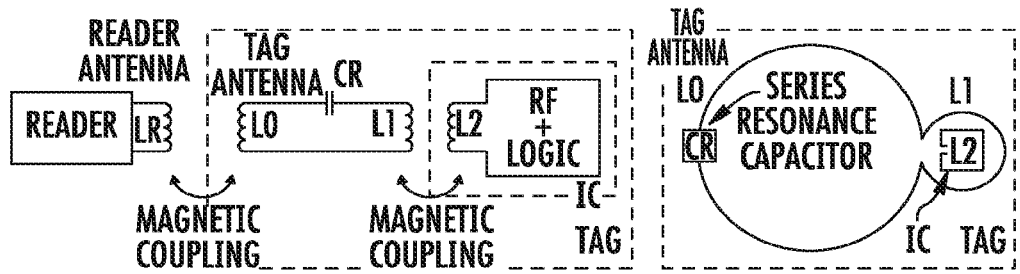
FIG. 2 shows a known device adapted to transmit in a contactless fashion the electromagnetic energy needed for the functioning of a buried sensor as in the prior art.
Figure 3:
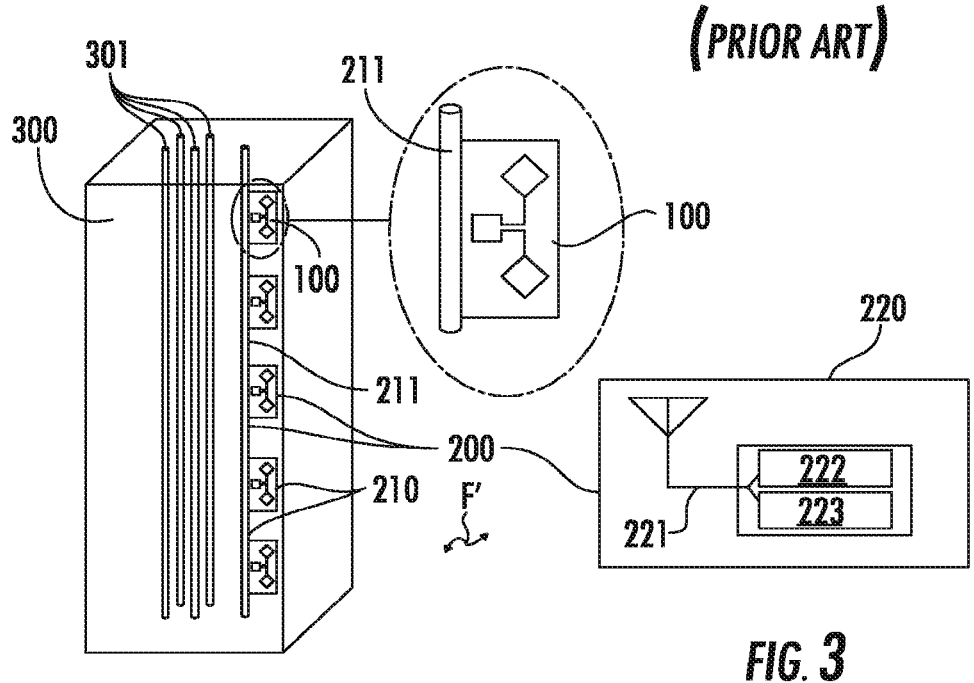
FIGS. 3 and 4 show known sensors adapted to receive in a contactless fashion electromagnetic energy, arranged in succession spaced one from the other as in the prior art.
Figure 4:
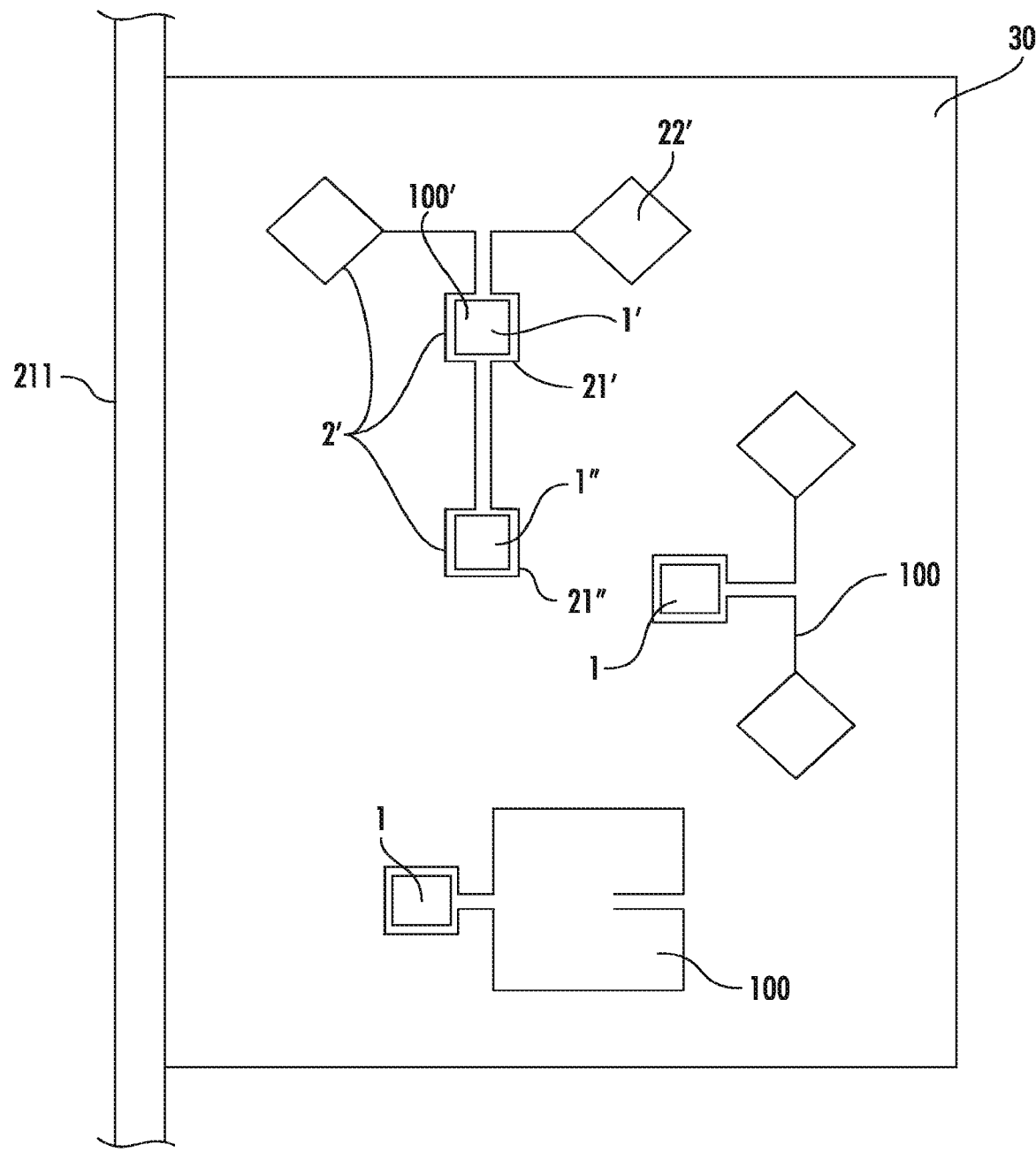
Figure 5:
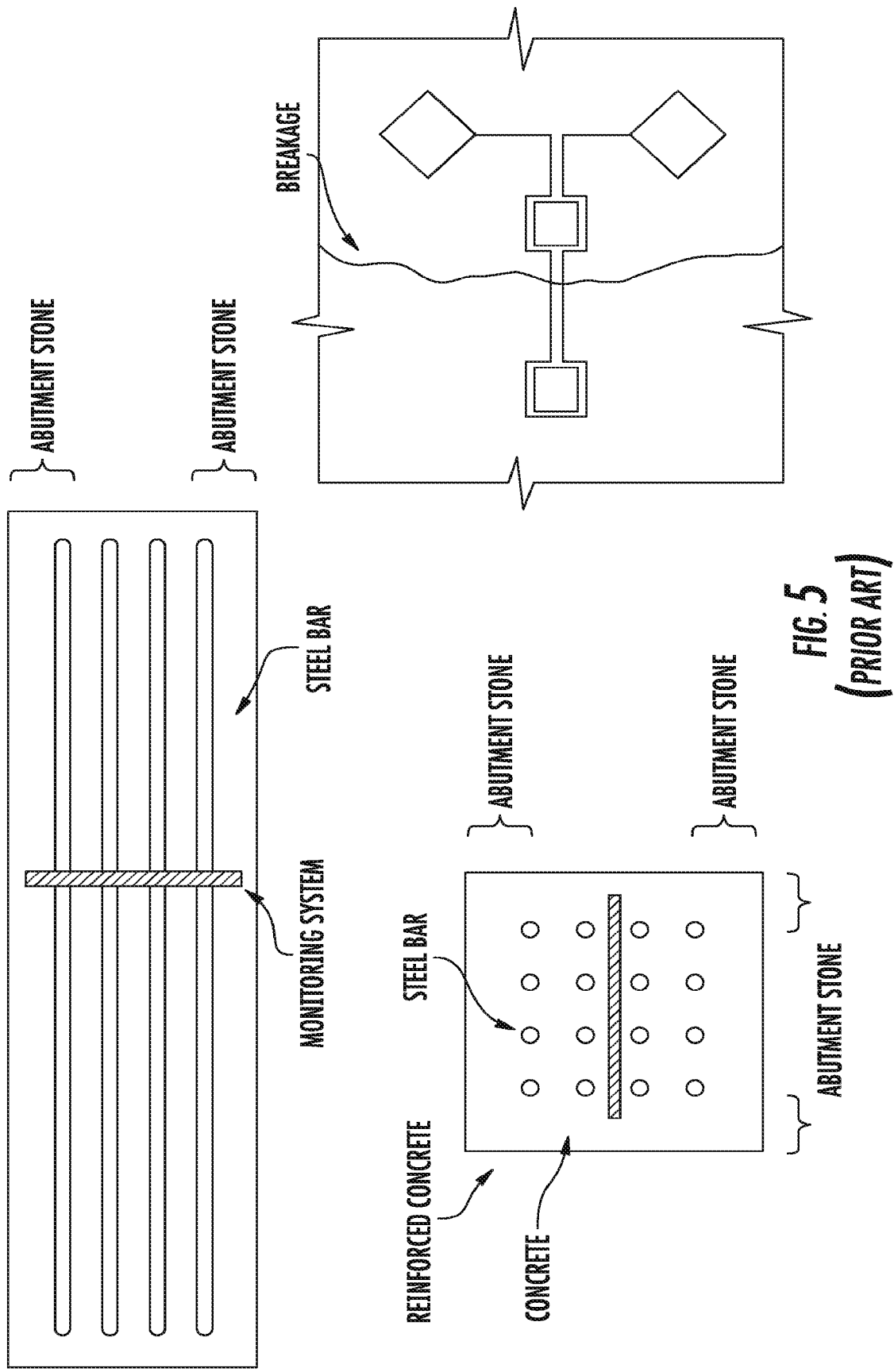
FIG. 5 shows a cover portion of a block of building material containing a device adapted to receive in a contactless fashion the electromagnetic energy required for operating a buried sensor as in the prior art.
Figure 6:
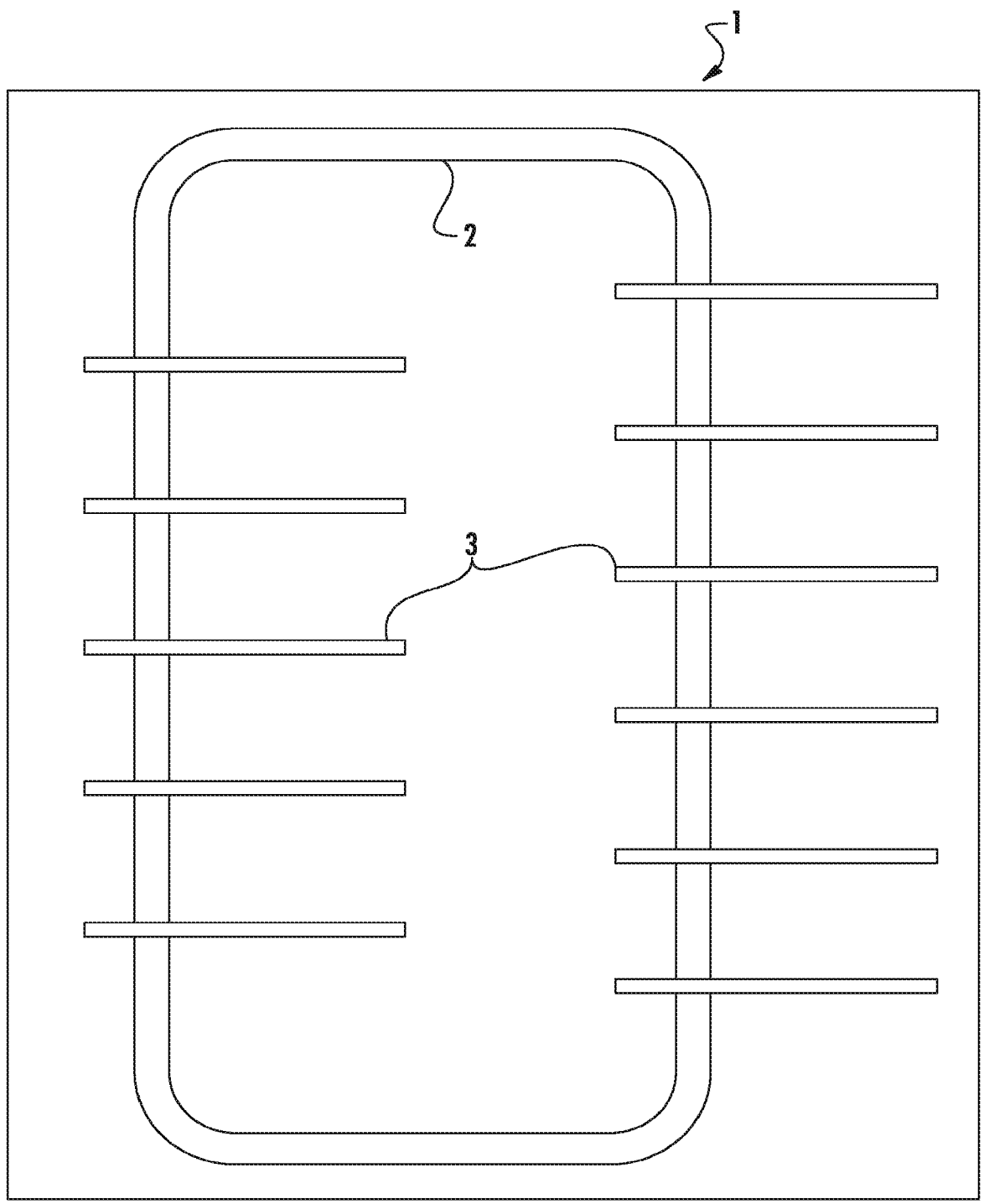
FIG. 6 illustrates an embodiment of the block of building material according to this disclosure containing a magnetic circuit and sensors magnetically coupled thereto.

An embodiment depicted in FIG. 6 shows the block of building material 1 containing a magnetic circuit 2 and sensing devices 3 of at least one physical characteristic of the building material, wherein these sensing devices 3 are magnetically coupled to the magnetic circuit 2. The magnetic circuit 2 may be wholly buried in the building material 1, as shown in FIG. 6, or only be partially buried, as will be illustrated hereinafter.

Figure 7:
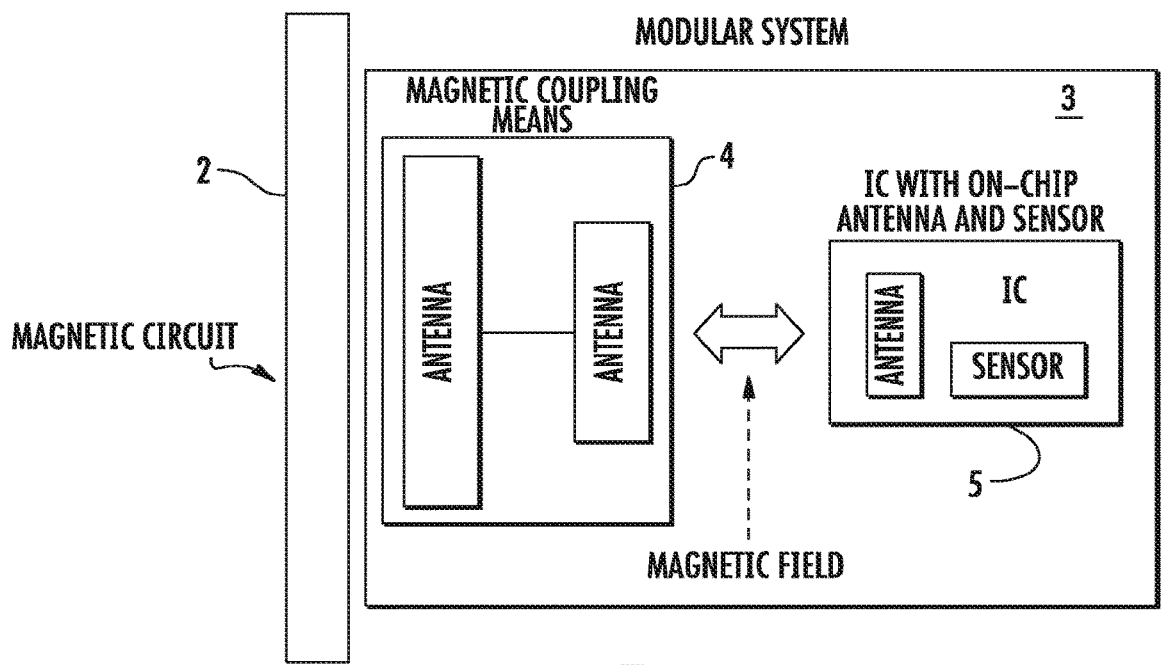
FIG. 7 shows how to magnetically couple a device as disclosed in the US patent application No. 2009/0033467 and the PCT application WO 2012/084295 to the buried magnetic circuit.

Sensing devices 3 adapted to be buried in a block of building material, such as, for example, the ones disclosed in the Italian patent application ITMI20102365 or the PCT patent application WO2012/084295 in the name of the same applicant and shown in FIG. 7, are magnetically coupled with the magnetic circuit 2. By inducing a variable magnetic field throughout the magnetic circuit 2, the circuit for power supplying and for contactless communications 4 generates an induced supply voltage of the sensor IC 5, that may operate also without electric connections with the external world.

The Patent publication WO2012/084295 discloses a technique that contemplates installing in the building material, starting from the cover portion, devices that; operating as contactless connections 4, are adapted to transmit energy of a supply electromagnetic field to the sensors IC 5 of the buried sensing devices 3, that were shielded by the cover portion itself and by the reinforcing metal structure, that act as a Faraday cage, buried in the building material. By contrast, according to the technique of the present disclosure, a structure is used that is preferably though not exclusively closed to form a magnetic circuit 2 for remotely supplying the sensors IC 5 of the buried sensing devices 3, without using the devices of the patent application WO2012/084295 that acted as contactless connections buried in the cover portion or without using dedicated electric supply lines of the sensing devices.

Even in case of destructive events such as fire or earthquakes, in which the cover portion may be damaged, it will still be possible to induce a variable magnetic field in the magnetic circuit and thus to supply the buried sensors IC 5. Eventual damage to the magnetic circuit, such as, for example, oxidation or even small interruptions, will eventually cause a thin gap that will increase the total reluctance of the magnetic circuit, but it will not hinder an external excitation coil to induce a variable magnetic field of intensity sufficient to supply at least one of the buried sensors. Different ways of generating a variable magnetic field inside the magnetic circuit 2 are possible. Only for example, some of them are illustrated in figures from 8 to 12.

Figure 8:
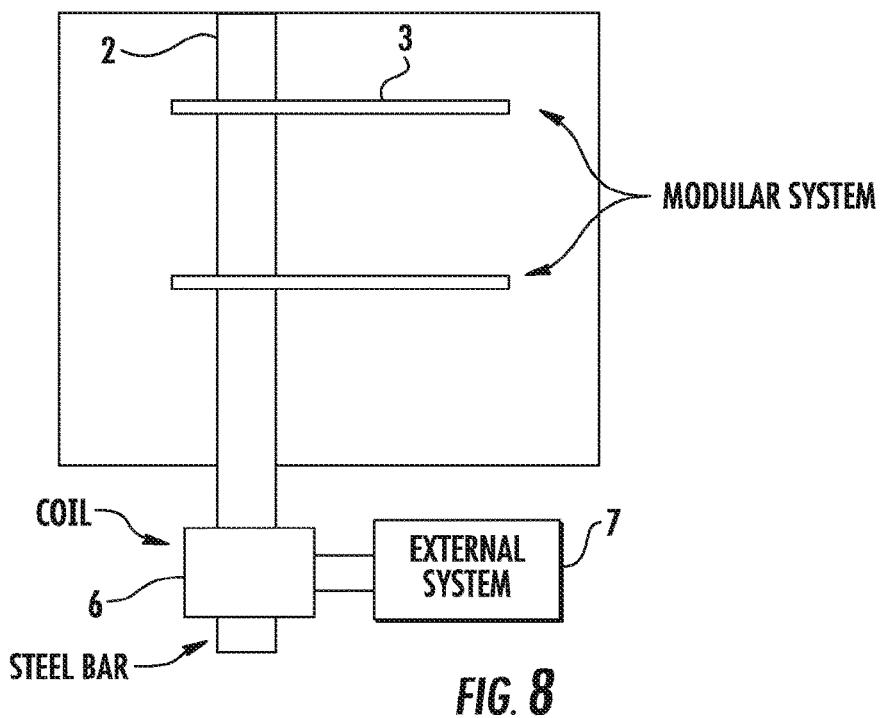
FIGS. 8 to 12 depict alternative embodiments for exciting a variable magnetic field in the magnetic material of the magnetic circuit buried in the block.

If the magnetic material of the magnetic circuit 2 is not fully buried in the building material, as shown in FIG. 8, it is possible to connect an excitation coil 6 to a unit 7, that will typically contain a generator configured for forcing a current throughout the excitation coil 6 and, optionally, transceiving circuits of signals from/to the sensing devices 3 buried and coupled to the magnetic circuit 2, and optionally, it may contain systems for collecting and analyzing data coming from the sensing devices 3.

Figure 9:
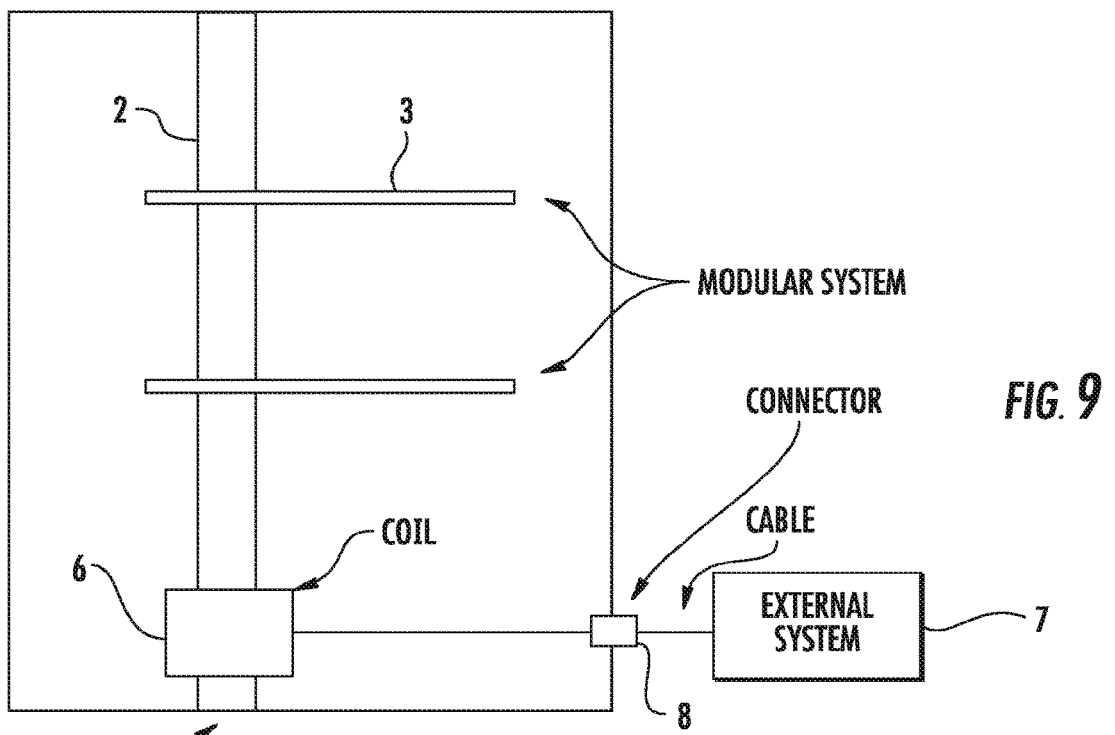

As an alternative, as shown in FIG. 9, the excitation coil 6 may be buried in the building material and be connected with the external unit 7 through wires equipped with electric connectors 8 protruding out of the block.

Figure 10:
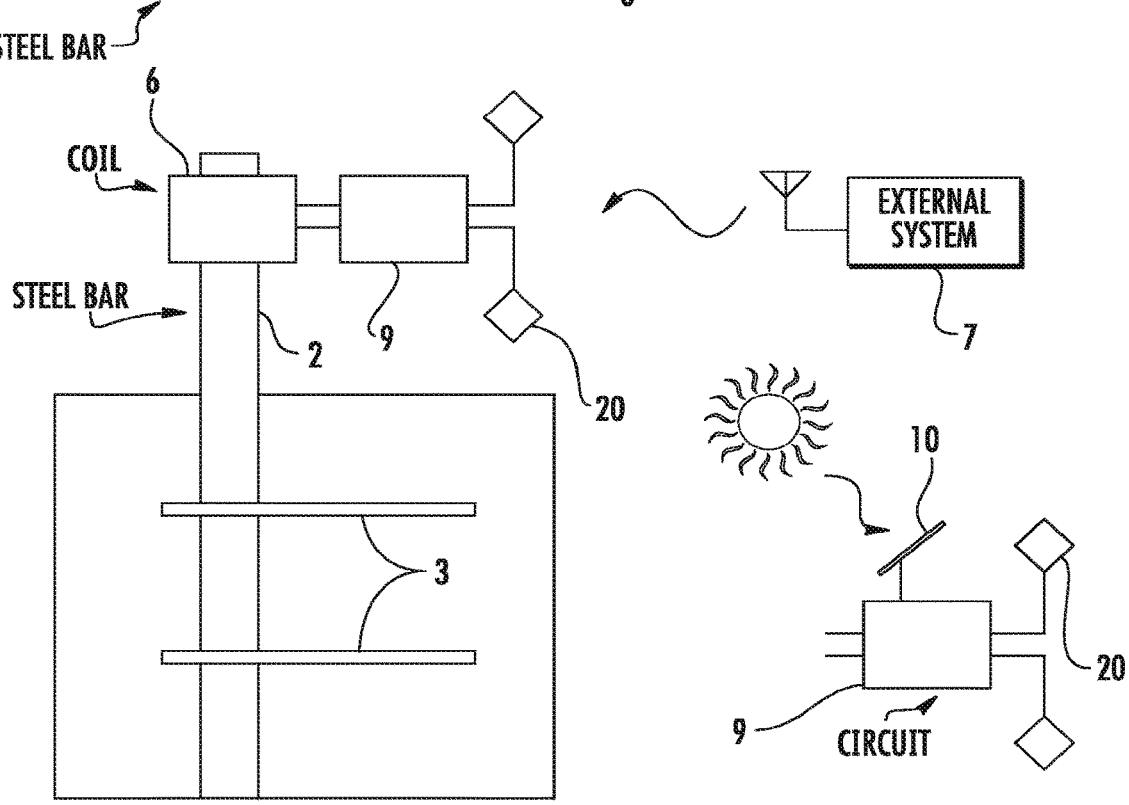
Figure 11:
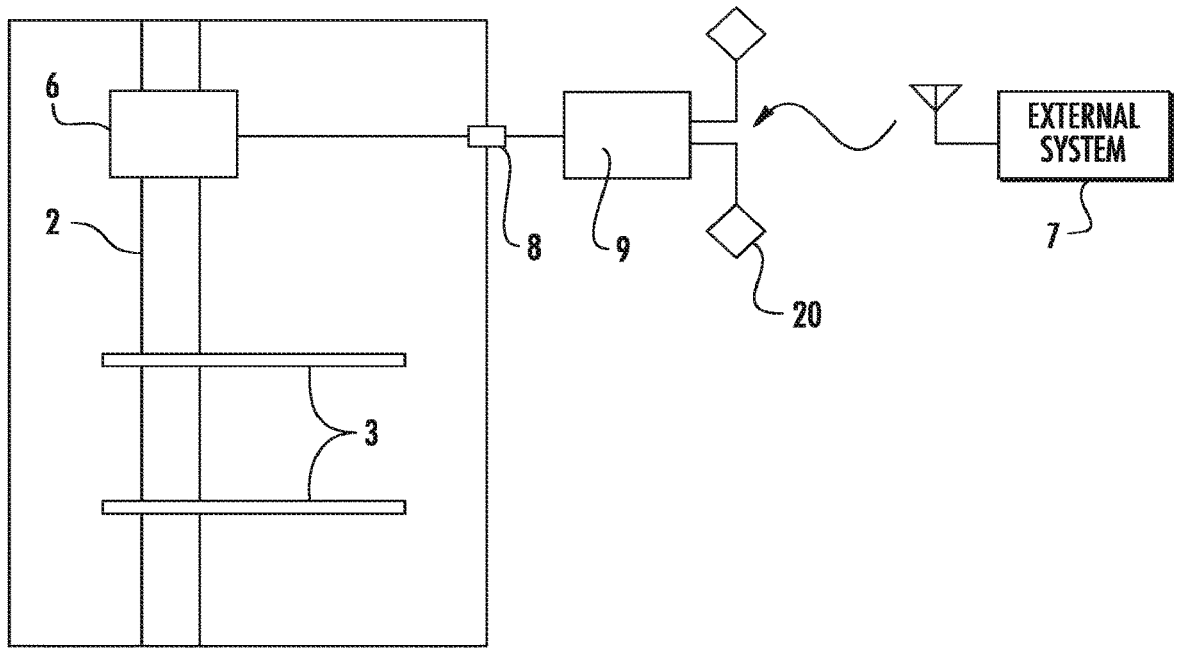

As shown in FIGS. 10 and 11, to supply the excitation coil 6, it is possible to use a circuit 9 equipped with an antenna 20 for remotely powering the system comprising the magnetic circuit 2 and of the sensing devices 3, to force a current throughout the coil 6 starting from an electromagnetic field irradiated by the antenna of the unit 7 and picked up by the antenna of the circuit 9. Optionally, the circuit 9 may be equipped with photovoltaic cells 10 to force an electric current throughout the coil 6 even when the unit 7 is not present or does not produce any electromagnetic fields, or does not produce a sufficiently intense magnetic field. Optionally, the circuit 9 may be equipped with batteries and/or accumulators for storing energy, that may be, for example, used during the night. Optionally, the circuit 9 may be equipped with circuits for collecting data coming from buried sensors IC 5 that are transmitted, also successively, to the unit 7.

Figure 12:
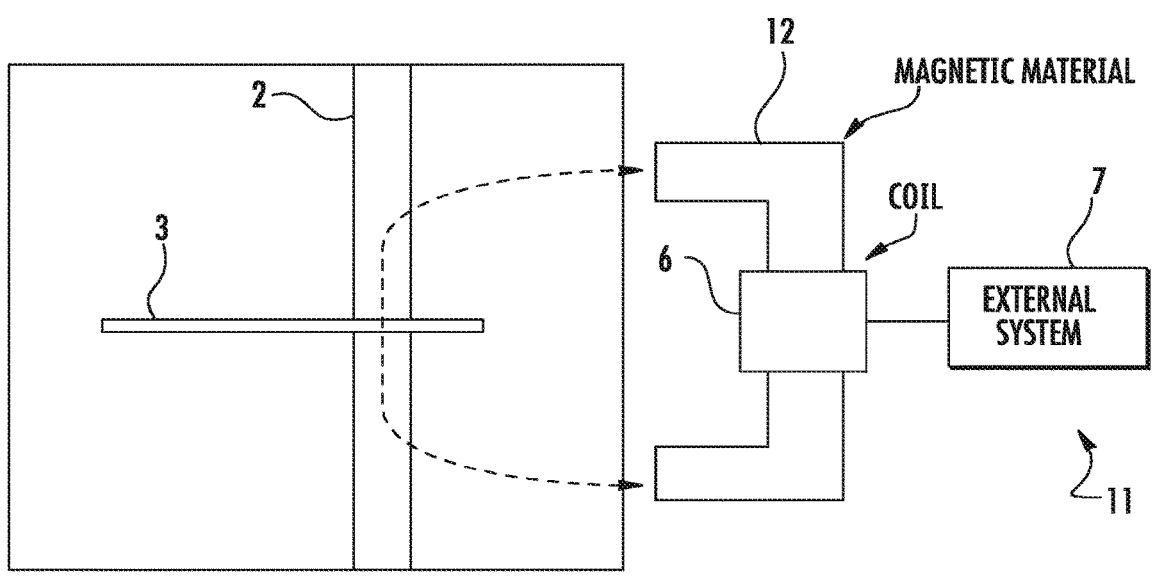

According to an aspect of the present disclosure, the sensing devices 3 may be powered as shown in FIG. 12, by using an excitation device ii comprising a magnetic material 12, for example, shaped as a horseshoe, in which a variable magnetic field is excited by the coil 6 powered by the unit 7. By moving the horseshoe shaped magnetic material 12 toward the magnetic circuit 2, a variable magnetic field is induced in the latter, thus allowing powering at least one sensing device 3. This may be useful for carrying out local measurements of parameters of the building structure for evaluating its health state in specific areas. These excitation devices ii are used in magnetometry, for measuring variations of reluctance of magnetic circuits, and in metal detectors. Any skilled person is capable of realizing such an excitation device ii using the above description and what is commonly known in the art, and for this reason its practical realization will not be described further.

Figure 13:
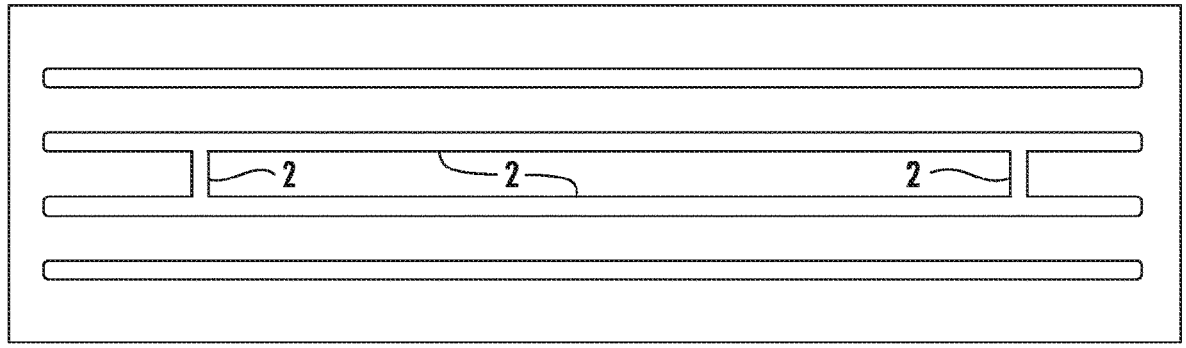
FIG. 13 illustrates and embodiment of the magnetic circuit according to this disclosure realized by connecting steel bars buried in the block and eventually coated by an external layer of magnetic material.

The magnetic circuit 2 may be realized by connecting among them steel reinforcing bars buried in the block, as shows in FIG. 13. This embodiment may be easily implemented by soldering among them the steel bars already present in a structure of the reinforced concrete. Because of the physical characteristic of magnetic reluctance of the bars, the illustrated embodiment may be conveniently used for conveying variable electromagnetic fields at relatively low frequencies.

Figure 14:
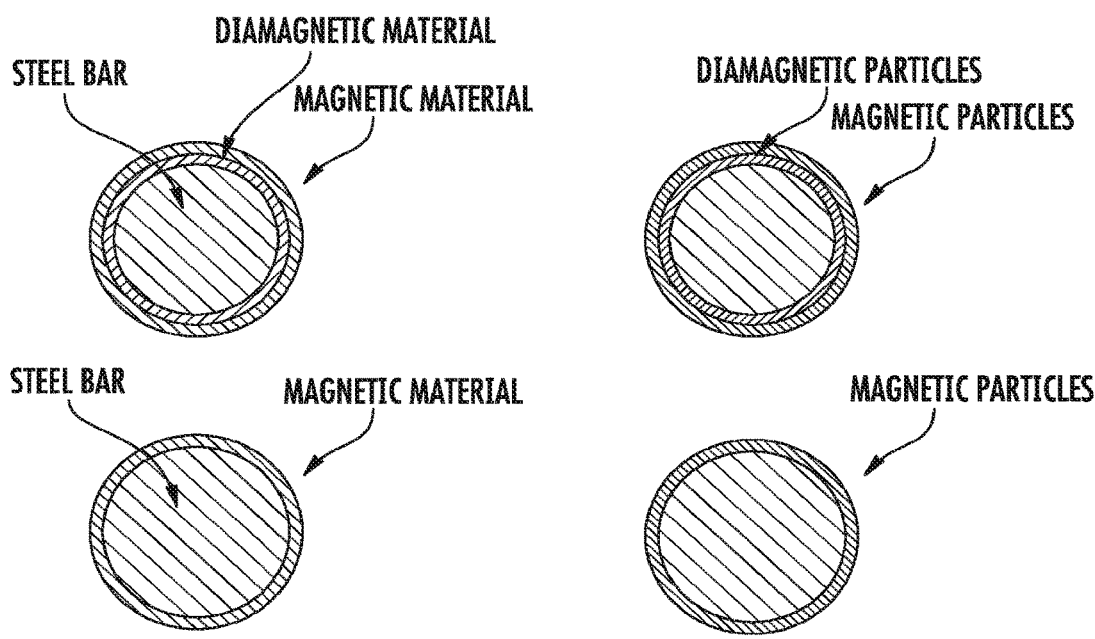
FIG. 14 show cross-sections of embodiments of steel bars coated by an external layer of magnetic material adapted to be used for realizing the magnetic circuit illustrated in FIG. 13.

In order to reduce the reluctance of the magnetic field at medium/high frequencies, conveniently the bars may be coated with a thin superficial layer of magnetic material, preferably a soft-magnetic material, that is a material that has a relatively narrow cycle of hysteresis with a negligible residual magnetization, as shown in FIG. 14. In this way, it will be possible to supply and communicate with sensing devices buried at relatively great distances by using variable electromagnetic fields at medium/high frequency.

Conveniently, in order to reduce the parasitic currents and the related losses, the steel bars may be coated with a layer of diamagnetic material which, in turn, is coated with the superficial layer of magnetic or soft-magnetic material. The diamagnetic material reduces the magnetic flux throughout the steel bars and conveys this magnetic flux throughout the magnetic material that covers the diamagnetic material.

Just as an example, the magnetic or soft-magnetic material may be chosen among cobalt, nickel, iron and alloys thereof, and may be deposited on the iron bars that define the magnetic circuit 2 by using traditional techniques. In the case in which this magnetic or soft-magnetic material is in the form of particles, it may be deposited, for example, with a paint or a spray.

Figure 15:
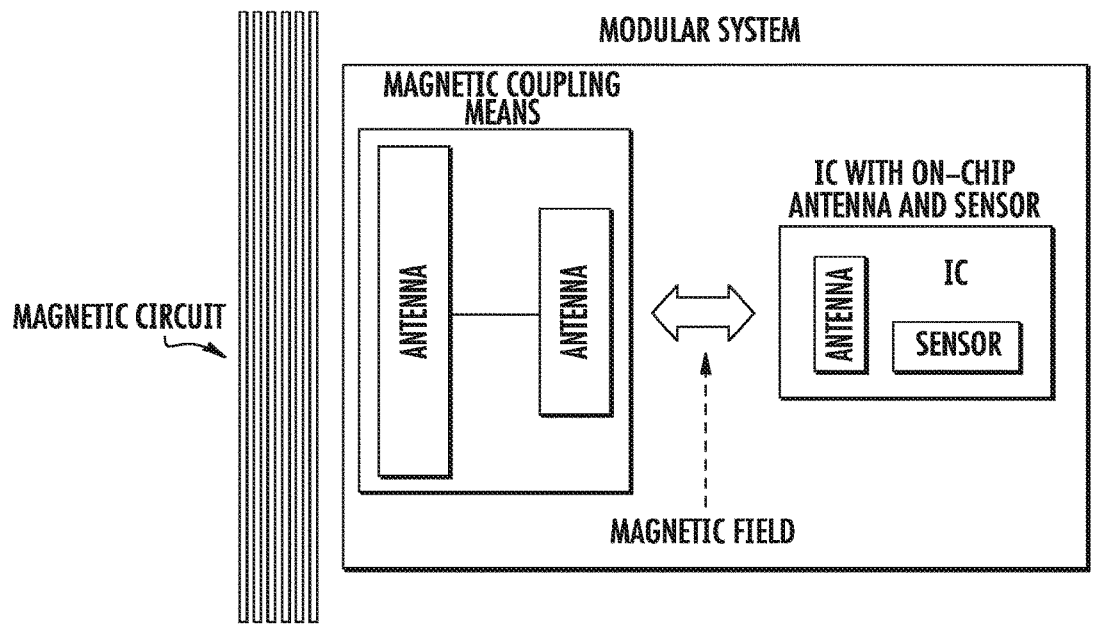
FIG. 15 depicts an embodiment of the magnetic circuit according to this disclosure realized with wire threads coated with a magnetic material.
Figure 16:
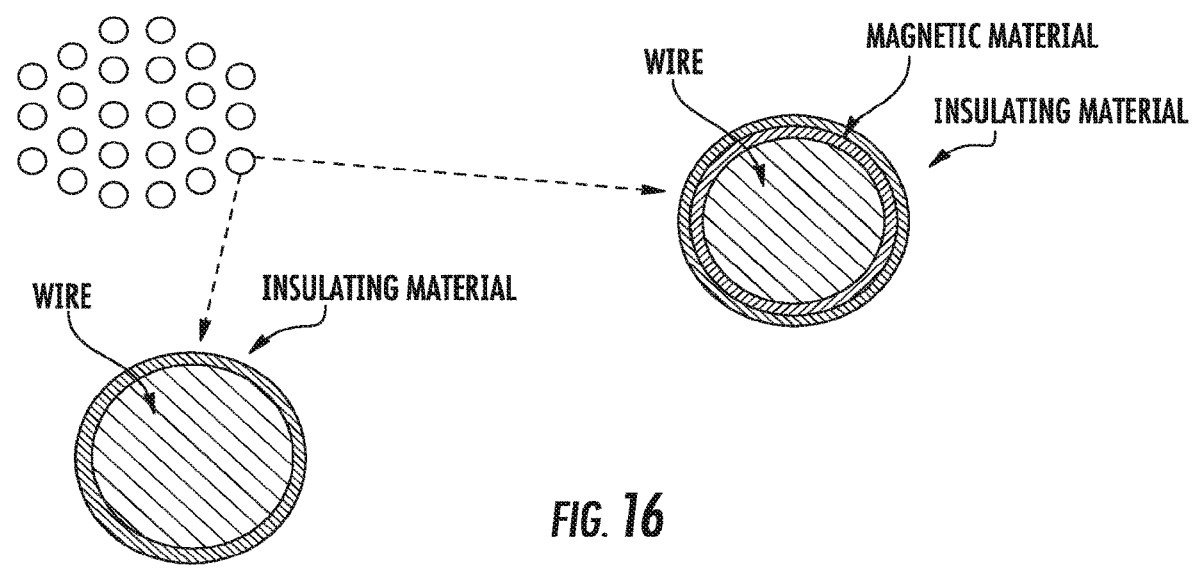
FIG. 16 shows embodiments of coated steel threads adapted to be used for realizing the magnetic circuit illustrated in FIG. 15.

In order to reduce further the losses due to parasitic currents and thus allow making buried sensors IC 5 work at relatively high frequencies, according to an embodiment the magnetic circuit 2 will be provided, as schematically shown in FIG. 15, by wire threads of magnetic material or, as shown in FIG. 16, by wire threads coated with a magnetic material. This will make the flexible magnetic circuit adapted to form magnetic circuits even along curved paths that may be very complex, for carrying out measurements of parameters of the building structure even in specific zones.

Optionally, the threads may be coated with a layer of isolating material in order to reduce eddy currents, and eventually the wire threads may be twisted to form a wire rope.

According to other embodiments, shown in FIGS. 17 and 18, particularly adapted to convey variable magnetic fields at high frequencies, the magnetic circuit 2 may be realized by rolling a sheet of isolating material 13 on which there is a uniform (FIG. 17) or striped (FIG. 18) coating of magnetic or soft-magnetic material 14 and by burying the so rolled sheet in the building material while pouring concrete. The coating 14, deposited preferably but not exclusively with a thin film technology, preferably has a low reluctance because it comprises magnetic or soft-magnetic material, and will show losses because of eddy currents that are relatively small because of its reduced thickness.

The isolating material 13 may be a resin, a fibrous material or even a polymer, such as for example Teflon, Kapton, PEN, PET, Polymide or Arylite. Preferably, the layer of soft-magnetic material will have a thickness between 100 nm and 1 mm, more preferably between 0.5 and 2, even more preferably a thickness of 1 μm.

The sheet of isolating material 13 may be rolled keeping the surface coated with the layer of magnetic or soft-magnetic material oriented toward either the inside or the outside.

Tests carried out by the applicant showed that a magnetic circuit according to the embodiment of FIGS. 17 and 18 allows supplying sensing devices and transceiving data from/toward them at high frequencies also at distances of several tens of meters.

Figure 19:
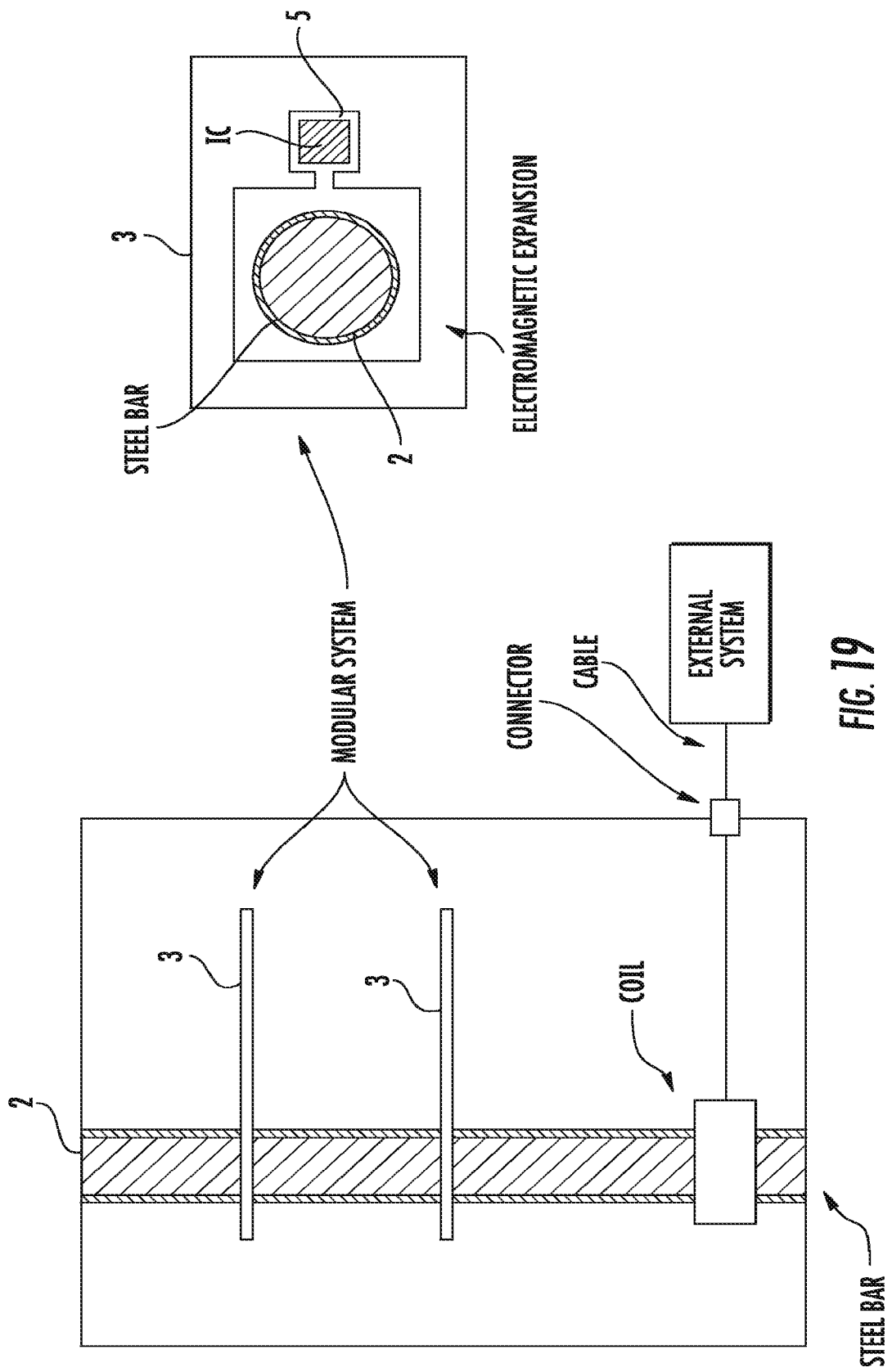
FIG. 19 shows a magnetic circuit comprising steel bars covered by an external layer of magnetic or soft-magnetic material and sensing devices magnetically coupled thereto according to this disclosure.

As shown in FIG. 19, the sensing devices 3 to be coupled to the magnetic circuit 2 may have a so-called circuit of electromagnetic expansion or concentration, configured such to be concatenated both with the magnetic circuit 2 and with the sensor IC 5 or sensing device IC. In the exemplary embodiment shown in FIG. 19, the steel bar is coated with a layer of magnetic or soft-magnetic material, to have a reduced reluctance. This allows enhancing the performance of the magnetic circuit by reducing the losses of the conveyed variable magnetic field and thus allows exchanging information with the sensing device IC even at relatively high frequencies.

Figure 20:
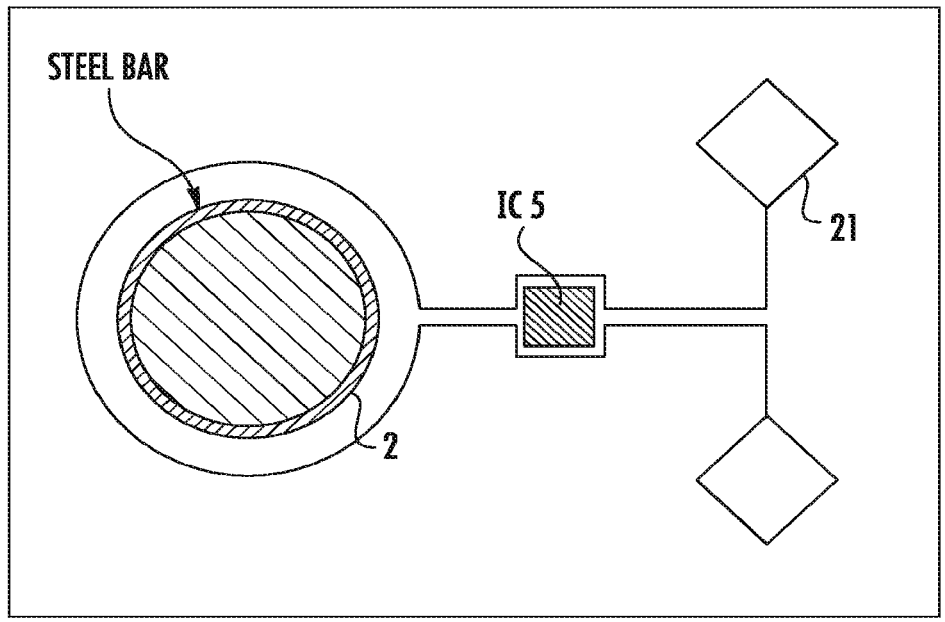
FIG. 20 shows and embodiment of a sensing device with an electromagnetic expansion antenna according to this disclosure.

In an embodiment shown in FIG. 20, the sensing device 3 is equipped with two electromagnetic expansion or concentration circuits, according to the disclosure in the US Patent publication No. 2009/0033467 and the PCT publication WO 2012/084295. In this way, the sensor IC 5 may be supplied and may communicate through the magnetic circuit 2 or through an antenna 21.

Different exemplary embodiments of sensing devices 3 of the power supply circuit, concatenated with the magnetic circuit 2, are shown in the figures from 21 to 30. For sake of ease, reference will be made to the case in which these devices are coupled to a magnetic circuit comprising steel bars of a block of reinforced concrete, though they may be used also in combination with a magnetic circuit 2 provided by a sheet of isolating material 13 coated with magnetic or soft-magnetic material, as shown in FIGS. 17 and 18, or provided by reinforcing bars coated with a superficial magnetic layer, as shown in FIG. 14, or yet to be provided by metal threads, as shown in FIG. 16.

Figure 21:
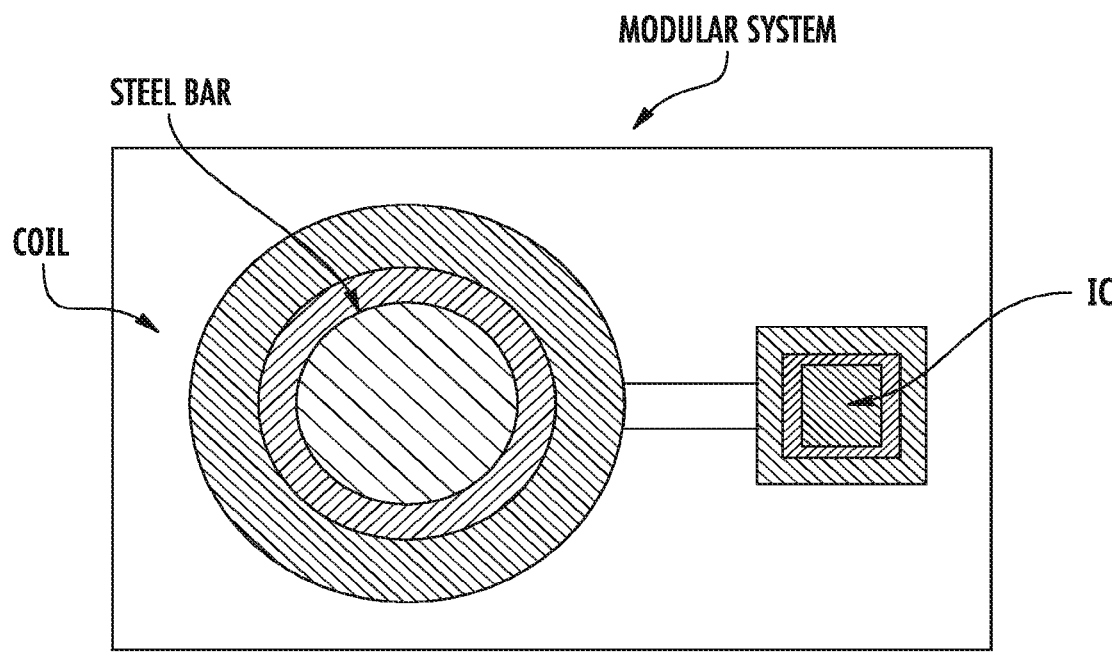
Figure 22:
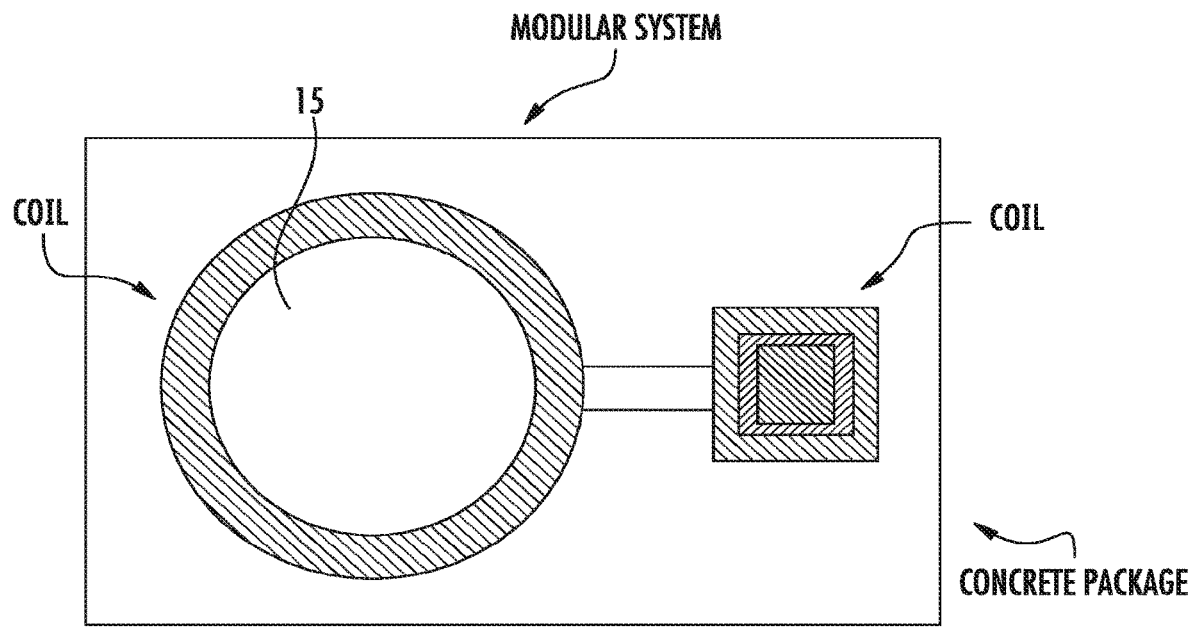

The sensor IC 5 may be directly buried in the block after mounting it on the magnetic circuit (FIG. 21), or may be enclosed in a package of building material (FIG. 22) such to form a solid block of relatively reduced size that embeds the electronic circuitry. This solid block will be mounted on the magnetic circuit before pouring concrete. In the embodiments shown in FIGS. 21 and 22, that are particularly adapted to low frequency communications, the coils COIL that couple the sensor IC to the magnetic circuit may be realized in discrete form, for example, by winding a conductive wire.

Figure 23:
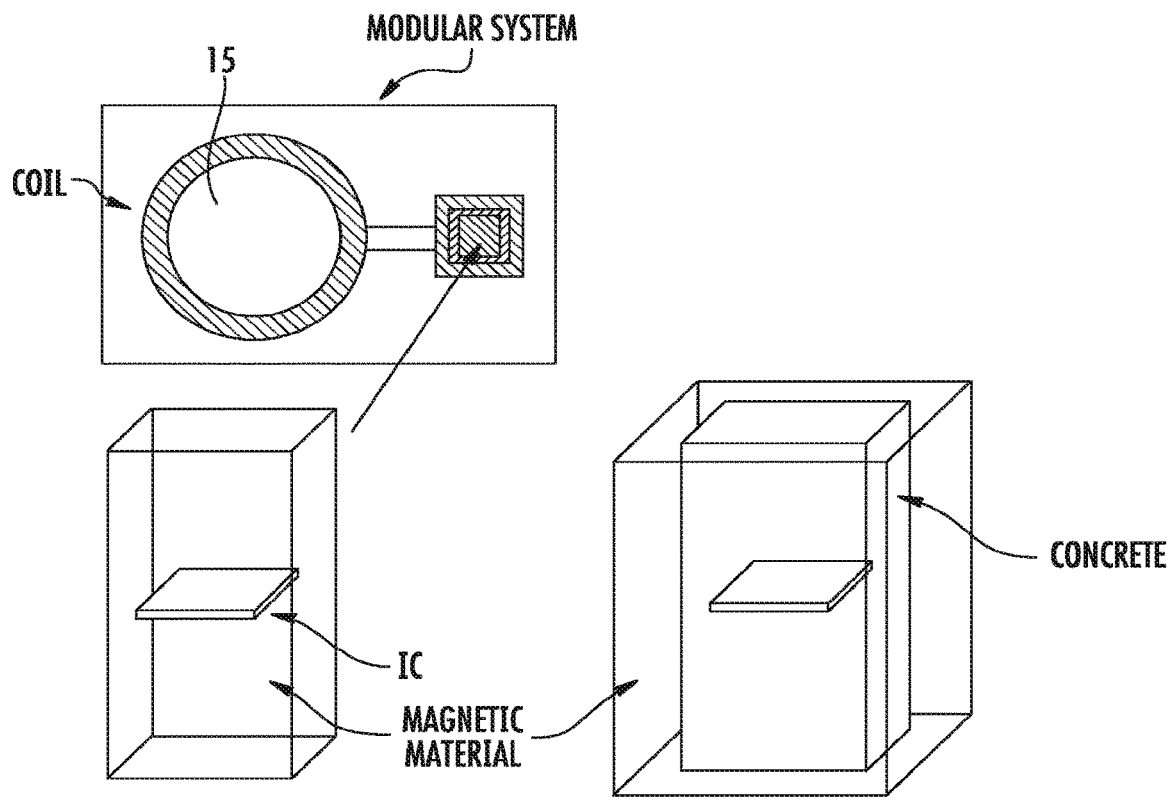

According to an embodiment, the sensor IC 5 may be inside a block of non-conducting magnetic material (FIG. 23), for example, of ferrite. According to an embodiment, the sensor IC may be buried in a package of building material 22, which, in turn, is embedded in the block of magnetic material. The block of magnetic material that surrounds the sensor IC 5 will offer a low reluctance to the concatenated magnetic field with the windings, enhancing energy transfer from the magnetic circuit 2 buried in the block and the coil that supplies the sensor IC.

The sensing device 3 with the electromagnetic expansion or concentration circuit may be realized on a flexible support and may be shaped as in FIG. 24, with an internal hole 15, of a size adapted to house a reinforcing bar buried in the block of building material, and equipped with flexible wings 23 for fixing the device to the reinforcing bar without soldering or without using bolts. The device shown in FIG. 24 will be installed on the steel bars before the final soldering, for forming a closed magnetic circuit.

Figure 25:
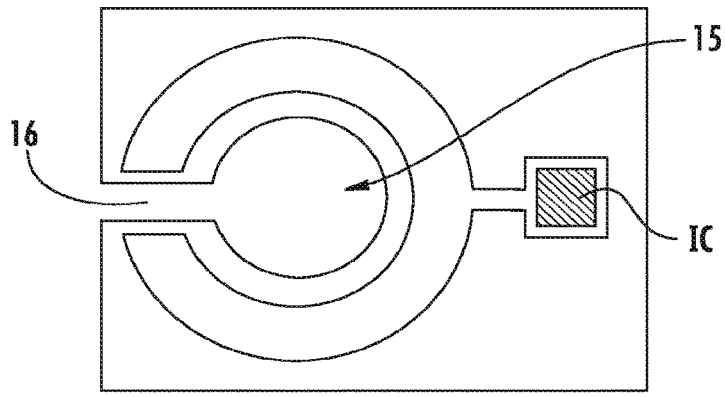
Figure 26:
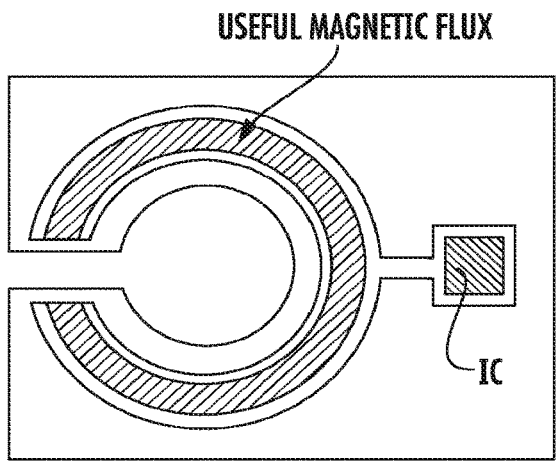

An alternative embodiment of the buried sensing device 3 is shown in FIG. 25. In this embodiment, the substrate of the electromagnetic expansion or concentration circuit is made of flexible material and is substantially C-shaped such to define a hole 15, of a size adapted to be crossed by the magnetic circuit, with a slit 16. The so shaped device may be fixed to the magnetic circuit of the block at any time before pouring the building material, thus not necessarily before realizing the magnetic circuit, for example, by soldering among them the steel bars, simply by elastically enlarging the slit 16 to force the material of the magnetic circuit to enter in the hole 15. The electromagnetic expansion circuit is defined on the substrate to be subjected to a flux of a magnetic field (FIG. 26) concatenated with at least a part of the magnetic circuit 2 threaded in the hole 15.

Figure 27:
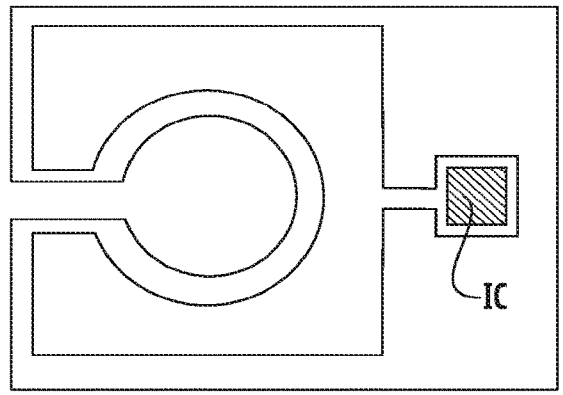

The electromagnetic expansion circuit may have any shape, for example as shown in FIG. 27, provided that it is crossed by a flux of a magnetic field.

Figure 28:
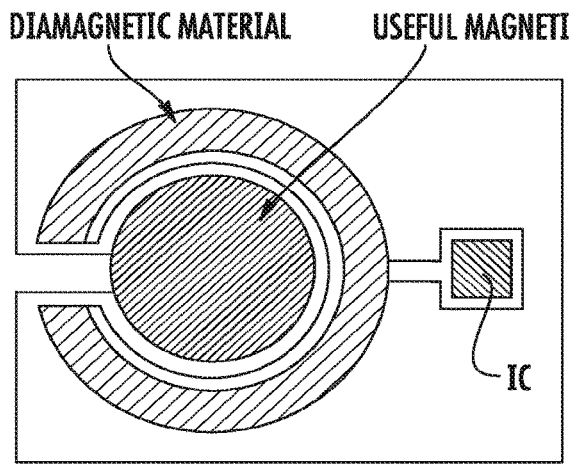
Figure 29:
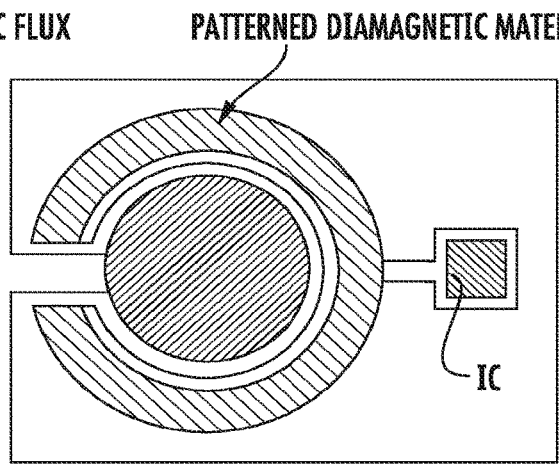

According to alternative embodiments shown in FIGS. 28 and 29, the electromagnetic expansion circuit may be closed around a zone of the substrate containing diamagnetic material, eventually patterned, such as bismuth, graphite, or pyrolithic graphite. The function of the diamagnetic material is that of increasing the energy transferred from the magnetic circuit 2 to the sensing device 3.

According to an embodiment, the diamagnetic material may be patterned to reduce eddy currents.

According to yet another embodiment (FIG. 30), the substrate of the electromagnetic expansion circuit is equipped with holes, eventually threaded, in which blocks of magnetic or soft-magnetic material are inserted, eventually by screwing them. These blocks allow reducing the magnetic reluctance seen by the magnetic flux coupled with the magnetic expansion circuit. This characteristic allows more intense magnetic fluxes and thus enhances the magnetic coupling with the magnetic circuit 2 buried in the building material, thus allowing increased efficiency of energy transfer to the buried sensor IC 5.

These blocks may be made of plastic or of polymer within which there are particles of magnetic material. For example, these blocks may be shaped as a screw with its relative bolt.

What is claimed is:

1. A building structure comprising:
    a block of building material;
    a magnetic circuit comprising an excitation coil disposed outside the block of building material and a plurality of interconnected steel reinforcing bars buried in the block of building material, the plurality of interconnected steel reinforcing bars being coated with a layer of magnetic material; and
    a sensor disposed within the block of building material, the sensor being configured to determine pressure, a humidity, or a temperature of the block of building material, the sensor being coupled to the magnetic circuit and configured to be powered by the magnetic circuit.

2. The building structure of claim 1, wherein the block of building material comprises concrete.

3. The building structure of claim 1, wherein the magnetic circuit further comprises a roll of magnetic material disposed within a magnetically-isolating material.

4. The building structure of claim 3, wherein the magnetic circuit further comprises a uniform coating of magnetic material lining the magnetically-isolating material.

5. The building structure of claim 3, wherein the magnetically-isolating material comprises at least one of resins, fibrous materials, polymers, Teflon, Kapton, PEN, PET, Polymide, or Arylite.

6. The building structure of claim 1, wherein the sensor is buried in a package of the block of building material, the package being embedded in the block of magnetic material.

7. The building structure of claim 1, wherein the magnetic circuit comprises an expansion circuit comprising a C-shaped flexible substrate defining a hole and a slit through the expansion circuit.

8. The building structure of claim 7, wherein further comprising a magnetic or soft-magnetic material disposed in the hole.

9. The building structure of claim 1, wherein the magnetic circuit comprises an expansion circuit comprising a flexible substrate defining a hole housing one of the steel reinforcing bars.

10. A building structure comprising:
    a building material;
    a magnetic circuit comprising an excitation coil disposed within the building material, the magnetic circuit comprising a plurality of interconnected steel reinforcing bars buried in the building material, the plurality of interconnected steel reinforcing bars being coated with a layer of magnetic material and electrically coupled to the excitation coil; and
    a sensor disposed within the building material, the sensor being configured to determine pressure, a humidity, or a temperature of the building material, the sensor being coupled to the magnetic circuit and configured to be powered by the magnetic circuit; and a connector protruding out of the building material, the connector configured to be coupled to an external unit for powering the excitation coil.

11. The building structure of claim 10, wherein the magnetic circuit comprises a plurality of wire threads extending through at least a portion of the building material.

12. The building structure of claim 11, wherein each of the plurality of wire threads is coated with a magnetic material.

13. The building structure of claim 11, wherein the plurality of wire threads are twisted to form a wire rope.

14. The building structure of claim 10, wherein the magnetic circuit further comprises a roll of magnetic material disposed within a magnetically-isolating material, wherein the magnetic circuit further comprises a uniform coating of magnetic material lining the magnetically-isolating material.

15. The building structure of claim 10, wherein the magnetic circuit further comprises a roll of magnetic material disposed within a magnetically-isolating material, wherein the roll of magnetic material comprises a striped roll of magnetic material disposed within the magnetically-isolating material, wherein the striped roll of magnetic material comprises a plurality of spatially-separated segments.

16. The building structure of claim 10, further comprising an antenna circuit coupled to the connector, the antenna circuit disposed outside the building material and configured to remotely power the sensor.

17. The building structure of claim 10, further comprising an antenna circuit coupled to the connector, the antenna circuit disposed outside the building material and comprising photovoltaic cells to power the sensor.

18. The building structure of claim 10, wherein the magnetic circuit comprises an expansion circuit comprising a C-shaped flexible substrate defining a hole and a slit through the expansion circuit.

19. The building structure of claim 18, wherein further comprising a magnetic or soft-magnetic material disposed in the hole.

20. The building structure of claim 10, wherein the magnetic circuit comprises an expansion circuit comprising a flexible substrate defining a hole housing one of the steel reinforcing bars.

21. A system, comprising:
a plurality of sensing devices configured to determine pressure, a humidity, or a temperature of a material;
a circuit comprising a rolled sheet of magnetic material, the circuit being configured to have a contactless coupling with the plurality of sensing devices, the circuit being further configured to generate a variable magnetic field to supply power to the plurality of sensing devices; and
an excitation coil around at least a portion of the circuit, the excitation coil comprising supply terminals to provide a current flow through the excitation coil.

22. The system of claim 21, further comprising a building material, wherein the plurality of sensing devices and the circuit are at least partially buried in the building material, and wherein the plurality of sensing devices is configured to determine a pressure, a humidity, or a temperature of the building material.

23. The system of claim 21, wherein the rolled sheet of magnetic material comprises a uniform coating of the magnetic material over a magnetically isolating material.

24. The system of claim 21, wherein the rolled sheet of magnetic material comprises a striped coating of the magnetic material over a magnetically isolating material.

25. The system of claim 24, wherein the magnetically isolating material comprises at least one of resins, fibrous materials, polymers, Teflon, Kapton, PEN, PET, Polymide, or Arylite.

26. The system of claim 21, wherein the magnetic material comprises at least one of cobalt, nickel, iron or alloys thereof.

* * * * *